(12) United States Patent
Bissig et al.

(10) Patent No.: US 9,067,059 B2
(45) Date of Patent: Jun. 30, 2015

(54) LIGHT DELIVERY DEVICE

(76) Inventors: Alois Bissig, Flueelen (CH); Erich Zurfluh, Altdorf (CH); Andreas Rose, San Marcos, CA (US)

( * ) Notice: Subject to any disclaimer, the term of this patent is extended or adjusted under 35 U.S.C. 154(b) by 1065 days.

(21) Appl. No.: 12/369,801

(22) Filed: Feb. 12, 2009

(65) Prior Publication Data

US 2009/0204111 A1 Aug. 13, 2009

Related U.S. Application Data

(60) Provisional application No. 61/028,260, filed on Feb. 13, 2008.

(51) Int. Cl.
*A61N 5/067* (2006.01)
*A61N 5/06* (2006.01)
*A61B 18/22* (2006.01)

(52) U.S. Cl.
CPC ....... *A61N 5/0603* (2013.01); *A61B 2018/2261* (2013.01); *A61N 5/0601* (2013.01); *A61N 5/062* (2013.01); *A61N 5/0624* (2013.01); *A61N 2005/0644* (2013.01)

(58) Field of Classification Search
CPC ............... A61B 2018/2261; A61B 2018/2272; A61N 5/0601; G02B 6/0008; G02B 6/02
USPC .............................................. 385/31, 95–132
See application file for complete search history.

(56) References Cited

U.S. PATENT DOCUMENTS

| | | | |
|---|---|---|---|
| 4,936,663 A | | 6/1990 | Mori |
| 5,074,632 A | * | 12/1991 | Potter ............................. 385/31 |
| 5,190,536 A | * | 3/1993 | Wood et al. ...................... 606/16 |
| 5,248,311 A | * | 9/1993 | Black et al. ...................... 606/15 |
| 5,269,777 A | * | 12/1993 | Doiron et al. ...................... 606/7 |
| 5,303,324 A | * | 4/1994 | Lundahl ......................... 385/147 |

(Continued)

FOREIGN PATENT DOCUMENTS

| | | |
|---|---|---|
| DE | 3941706 C1 | 2/1991 |
| DE | 19739456 A1 | 3/1999 |

(Continued)

OTHER PUBLICATIONS

International Search Report dated May 14, 2008. PCT/US2009/033744.

(Continued)

*Primary Examiner* — Gary Jackson
*Assistant Examiner* — Scott T. Luan
(74) *Attorney, Agent, or Firm* — The Dobrusin Law Firm, PC

(57) ABSTRACT

A light delivery device comprising an optical fiber having a non-feature portion and a feature portion having features that force light to couple out radially from the feature portion and provide a desired radial light output pattern. A method of photodisinfection of a cavity comprising of providing this device, apply a photosensitizing composition to treatment site within the cavity, and inserting at least a portion of the device into the cavity; and applying light delivered by the device from a light source to the treatment site within the cavity at a wavelength absorbed by the photosensitizing composition so as to inhibit or eliminate microbes located at the treatment site. The present invention also includes a method of making the device and a treatment kit containing the device and a container containing a photosensitizing composition.

25 Claims, 7 Drawing Sheets

(56) References Cited

U.S. PATENT DOCUMENTS

| | | | |
|---|---|---|---|
| 5,337,381 A * | 8/1994 | Biswas et al. | 385/36 |
| 5,429,635 A | 7/1995 | Purcell, Jr. et al. | |
| 5,431,647 A * | 7/1995 | Purcell et al. | 606/16 |
| 5,496,308 A * | 3/1996 | Brown et al. | 606/15 |
| 5,530,780 A | 6/1996 | Ohsawa | |
| 5,536,265 A * | 7/1996 | van den Bergh et al. | 606/2 |
| 5,611,793 A | 3/1997 | Wilson et al. | |
| 5,671,314 A * | 9/1997 | Gregory et al. | 385/128 |
| 5,754,717 A * | 5/1998 | Esch | 385/31 |
| 5,946,441 A | 8/1999 | Esch | |
| 5,976,175 A * | 11/1999 | Hirano et al. | 607/89 |
| 6,004,315 A * | 12/1999 | Dumont | 606/15 |
| 6,071,302 A * | 6/2000 | Sinofsky et al. | 607/88 |
| 6,113,589 A | 9/2000 | Levy et al. | |
| 6,211,335 B1 | 4/2001 | Owen et al. | |
| 6,251,127 B1 | 6/2001 | Biel | |
| 6,315,775 B1 * | 11/2001 | Thielen et al. | 606/16 |
| 6,366,719 B1 * | 4/2002 | Heath et al. | 385/31 |
| 6,398,778 B1 * | 6/2002 | Gu et al. | 606/15 |
| 6,551,346 B2 | 4/2003 | Crossley | |
| 6,576,163 B2 * | 6/2003 | Mersch | 264/1.1 |
| 6,583,117 B2 | 6/2003 | Owen et al. | |
| 6,602,274 B1 | 8/2003 | Chen | |
| 6,607,522 B1 | 8/2003 | Hamblin et al. | |
| 6,622,049 B2 | 9/2003 | Penner et al. | |
| 2001/0047195 A1 * | 11/2001 | Crossley | 607/88 |
| 2003/0128944 A1 * | 7/2003 | Skutnik | 385/123 |
| 2003/0167033 A1 | 9/2003 | Chen et al. | |
| 2003/0180224 A1 | 9/2003 | Brown et al. | |
| 2004/0030368 A1 * | 2/2004 | Kemeny et al. | 607/88 |
| 2004/0147508 A1 | 7/2004 | Brown et al. | |
| 2005/0022610 A1 * | 2/2005 | Leys et al. | 73/861.57 |
| 2005/0094947 A1 * | 5/2005 | James et al. | 385/88 |
| 2005/0107853 A1 | 5/2005 | Krespi et al. | |
| 2005/0131400 A1 * | 6/2005 | Hennings et al. | 606/15 |
| 2005/0137587 A1 * | 6/2005 | Nield et al. | 606/15 |
| 2006/0047329 A1 | 3/2006 | Krespi et al. | |
| 2006/0093561 A1 | 5/2006 | Kennedy | |
| 2006/0104593 A1 * | 5/2006 | Gowda et al. | 385/140 |
| 2006/0194164 A1 | 8/2006 | Altshuler et al. | |
| 2007/0179488 A1 * | 8/2007 | Trusty et al. | 606/16 |
| 2007/0255356 A1 | 11/2007 | Rose et al. | |
| 2008/0119914 A1 | 5/2008 | Rose et al. | |
| 2008/0269845 A1 | 10/2008 | Rose et al. | |

FOREIGN PATENT DOCUMENTS

| | | |
|---|---|---|
| DE | 19803460 C1 | 8/1999 |
| DE | 10210007 A1 | 10/2003 |
| EP | 0437183 A | 7/1991 |
| EP | 0450149 A | 10/1991 |
| EP | 0672435 A | 9/1995 |
| EP | 0761257 A | 3/1997 |
| RU | 2235568 | 9/2004 |
| WO | 9904857 A | 2/1999 |
| WO | 03/084601 A | 10/2003 |
| WO | 2004/093760 A | 11/2004 |
| WO | WO2006063847 | 3/2006 |
| WO | 2006/115761 | 11/2006 |

OTHER PUBLICATIONS www.puritanmedproducts.com Product #'s 4545 and 4620 mfg. by Puritan Medical Products LLC, Maine., 2 pages, Oct. 19, 2007.
Co-Pending PCT application Serial # PCT/US07/67583, filed Apr. 27, 2007, published as WO2007/127894.
Co-Pending U.S. Appl. No. 11/741,627, filed Apr. 27, 2007.
http://www.emedicine.com/ent/topic362.htm Billings, Kathleen R., Ototopical Antibiotics, Last Updated Mar. 21, 2001. 9 pages.
Co-Pending U.S. Appl. No. 11/741,584, filed Apr. 27, 2007.

* cited by examiner

LIGHT DELIVERY DEVICE

CLAIM OF BENEFIT OF FILING DATE

This application claims the benefit of U.S. Provisional Application Ser. No. 61/028,260 titled: "Light Delivery Device" filed on Feb. 13, 2008 and PCT Application No. PCT/US09/33744 titled: "Light Delivery Device" filed on Feb. 11, 2009.

FIELD OF INVENTION

The present invention relates to a light delivery device that provides a radial light output pattern especially useful for photodisinfection and methods of making and using such device to inhibit or eliminate microbes in a cavity, especially a body cavity.

BACKGROUND OF THE INVENTION

Sources of infective microbes are prevalent throughout our environment. A body cavity is naturally colonized with an enormous number of microbes usually kept in check by normal metabolism and an intact immune system. With the breakdown of the immune system, microbes cause infections. Antibiotics are generally used to treat such infections, but many microbes are becoming resistant to antibiotic treatments. Accordingly, there is a need to treat infections and decolonize microbes residing in body cavities without the use of antibiotics.

Photodisinfection can meet the need to treat infections and decolonize microbes residing in body cavities without the use of antibiotics. Photodisinfection is the use of a photosensitizing composition activated by light to inhibit or eliminate microbes. Specially designed light delivery devices have been invented to specifically provide the desired illumination pattern for photodisinfection of various body cavities. See U.S. Patent Application Publication No. US2007/0255356 and PCT Application No. PCT/US07/67583 both titled: Photodisinfection Delivery Devices and Methods, and are both incorporated by reference in their entirety.

SUMMARY OF THE INVENTION

The present invention provides a light delivery device comprising: an optical fiber having a non-feature portion and a feature portion having features that force light to couple out radially from the feature portion and provide a desired radial light output pattern. The radial light output pattern that can be provided by the light delivery device is especially useful for photodisinfection of a cavity, such as a body cavity.

The present invention provides a treatment kit for photodisinfection of a cavity comprising: the above-described light delivery device; a photosensitizing composition contained in a fluid source; and an application tip.

The present invention further provides a method of photodisinfection of a cavity comprising: providing the above-described light delivery device; applying a photosensitizing composition to treatment site within the cavity; inserting at least a portion of the device into the cavity; and applying light delivered by the device from the light source and via the waveguide to the treatment site within the cavity at a wavelength absorbed by the photosensitizing composition so as to inhibit or eliminate microbes located at the treatment site.

The present invention also provides a method to make a light delivery device comprising: providing an optical fiber having a non-feature portion and a feature portion; cutting features into the feature portion wherein the features are adapted to force light to couple out radially from the feature portion in a desired radial light output pattern.

BRIEF DESCRIPTION OF THE DRAWINGS

The features and inventive aspects of the present invention will become more apparent upon reading the following detailed description, claims, and drawings, of which the following is a brief description:

DESCRIPTION OF THE PREFERRED EMBODIMENT

I. Definitions

Figure 1:
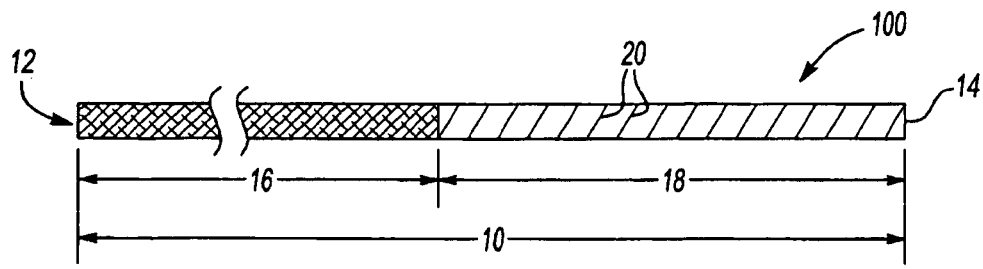
FIG. 1 is a side view of an exemplary embodiment of a device according to the present invention.
Figure 2:
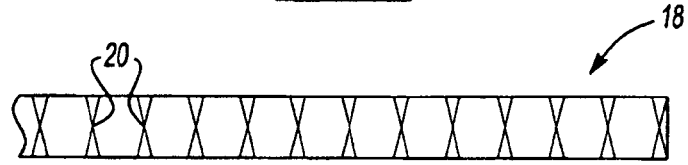
FIG. 2 is a side view another exemplary embodiment of the feature portion of the device shown in FIG. 1.
Figure 3:
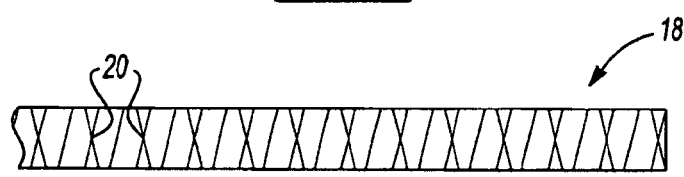
FIG. 3 is a side view of yet another exemplary embodiment of the feature portion of the device shown in FIG. 1.
Figure 4:
FIG. 4 is a side view of another exemplary embodiment of the feature portion of the device shown in FIG. 1.
Figure 5:
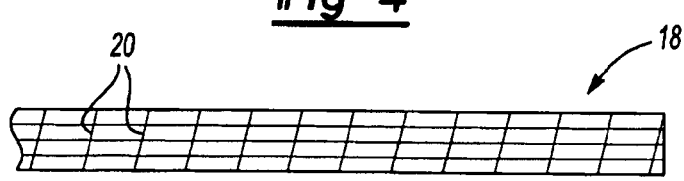
FIG. 5 is a side view of yet another exemplary embodiment of the feature portion of the device shown in FIG. 1.

The following terms are intended to have the following general meanings as they are used herein:

1. Body cavity: any cavity within a body such as ear, nose, vagina, lung, the entire digestive track (e.g., throat, esophagus, stomach, intestines, rectum, etc.), gall bladder, bladder, any open wound or the like. The body cavity can be within a human body or a body of another animal.

2. Light: light at any wavelengths that can be absorbed by a photosensitizing composition. Such wavelengths include wavelengths selected from the continuous electromagnetic spectrum such as ultraviolet ("UV"), visible, the infrared (near, mid and far), etc. The wavelengths are generally between about 100 nm to 10,000 nm, with exemplary ranges between about 160 nm to 1600 nm, between about 400 nm to about 900 nm, and between about 500 nm to about 850 nm, although the wavelengths may vary depending upon the particular photosensitizing compound used and the light intensity. Depending on the application, the light produced may be a single wavelength or multiple wavelengths.

3. Microbes: any and all disease-related microbes such as virus, fungus, and bacteria including Gram-negative organisms, Gram-positive organisms or the like. Some examples of microbes include but are not limited to, *Staphylococcus aureus*, Methicillin-resistant *Staphylococcus aureus* ("MRSA"), *Escherichia coli* ("*E. coli*"), *Enterococcus fecalis* ("*E. fecalis*"), *Pseudomonas aeruginosa, Aspergillus, Candida*, etc.

4. Photosensitizing composition: a composition comprising at least one suitable art-disclosed photosensitizer that has at least an antimicrobial action upon application of electromagnetic energy of certain wavelength(s). Suitable photosensitizers include both Type I and Type II photosensitizers, where Type I photosensitizers produce a free radical upon the application of light and Type II photosensitizers produce singlet oxygen upon the application of light. While photosensitizers that have other modes of operation (e.g. generation of heat) are contemplated, those types discussed above are preferred. Suitable classes of compounds that may be used as antimicrobial photosensitizers include tetrapyrroles or derivatives thereof such as porphyrins, chlorins, bacteriochlorins, phthalocyanines, naphthalocyanines, texaphyrins, verdins, purpurins or pheophorbides, phenothiazines, etc., such as those described in U.S. Pat. Nos. 6,211,335; 6,583,117; and 6,607,522 and U.S. Patent Publication No. 2003-0180224. Preferred phenothiazines include methylene blue (MB), toluidine blue (TBO), and those discussed in U.S. Patent Publication No. 2004-0147508. Other preferred antimicrobial photosensitizers include indocyanine green (ICG). Combinations of two or more photosensitizers, such as MB and TBO or the like, are also suitable. The photosensitizer may be present in the photosensitizer composition in any suitable amounts. Examples are between about 0.001 percentage of total weight (wt %) and 10 wt %, between about 0.001 wt % and about 5 wt %, between about 0.001 wt % to about 1 wt %, and between about 0.001 wt % to about 0.1 wt %. The photosensitizing composition may optionally contain a therapeutic agent, which is any chemical, drug, medication, proteinaceous molecule, nucleic acid, lipid, antibody, antigen, hormone, nutritional supplement, cell or any combination thereof that helps ameliorate a condition. Preferred therapeutic agents include those that promote wound healing, have antimicrobial action, have anti-inflammatory action, and/or provide pain relief. The photosensitizing composition may also optionally contain carriers, diluents, or other solvents for the photosensitizer or other components of the composition and may be used to adjust the concentration of photosensitizer. The photosensitizing composition may be any suitable phase such as a liquid, gel, paste, putty, or solid. Preferably, the compositions has a viscosity low enough to flow into the treatment site while also having a viscosity high enough to maintain the composition within the treatment site. Further compositions that become liquid after application to the treatment site are contemplated such as those that melt or go into solution in the treatment site. Alternately, the composition may gel after application to the treatment site as a liquid; this would permit the composition to cover the treatment site effectively, while also maintaining the composition in the treatment site. The photosensitizers mentioned above are examples and are not intended to limit the scope of the present invention in any way.

A. Light Delivery Device for Photodisinfection

FIG. 1 illustrates one exemplary embodiment of a device 100 according to the present invention. The device 100 enables photodisinfection of a cavity including human's nasal cavity. The device 100 includes an optical fiber 10. The fiber 10 can be any suitable art-disclosed optical fiber such as a polymer optical fiber ("POF"), a plastic fiber, a plastic clad glass fiber, a HCS fiber, a glass fiber, a sapphire fiber, a photonic crystal fiber, a hollow fiber, or the like. The present invention also contemplates using multiple art-disclosed fibers as the fiber 10. The fiber 10 can be of any suitable size. Examples of suitable fiber size includes optical fiber that is greater than about 3 mm in diameter, from about 3 mm to about 200 um in diameter, from about 3 mm to about 50 um in diameter, from about 1.5 mm to 200 um in diameter, from about 1 mm to 200 um in diameter; less than about 400 um in diameter, and less than about 200 um in diameter.

Proximal end 12 of the fiber 10 is adapted to be in communication with a light source (not shown) allowing transmission of light from the light source via the fiber 10 to the device 100. The light source can be a separate unit or units in communication with the fiber 10. The light source can be any suitable art-disclosed light emitting device such as laser, light emitting diode ("LEDs"), incandescent source, fluorescent source, or a combination thereof. The output of the light source is preferably adjustable so that the operator can modify the wavelength, the power output, the size of illumination, or combinations thereof while carrying out the present method. For example, the wavelength of a laser may be adjusted to activate different photosensitizers in the photosensitizing composition. Alternately, the power of the light source may be increased or decreased after an application of light energy to the treatment area. In addition, the light source may comprise a temperature monitoring device so that overheating of the host tissues in and around the treatment area may be avoided. Suitable temperature monitoring devices may comprise an IR device, a fiber optic device, a thermocouple, or a combination thereof. The light source may optionally include a foot switch for turning the light source on and/or off. The light source may also optionally include a separate power supply.

Referring back to FIG. 1, the fiber 10 has a directional output of light toward its distal end 14 and can deliver the illumination wavelength(s) desired for photodisinfection. Generally, the light source and the fiber 10 can be employed to deliver light of any wavelength(s) including visible and invisible light. For example, the light source and the fiber 10 can be employed for delivering light having wavelengths between and/or including deep UV to Far IR. The wavelengths are generally between about 100 nm to 10,000 nm, with exemplary ranges between about 160 nm to 1600 nm, between about 400 nm to about 800 nm, and between about 500 nm to about 850 nm, although the wavelengths may vary depending upon the particular photosensitizing compound used and the light intensity. Depending on the application, the light produced may be a single wavelength or multiple wavelengths. In one embodiment, the light source and the fiber 10 can provide a single wavelength at one time. In another embodiment, the light source and the fiber 10 can provide two or more wavelengths at one time or sequentially.

Figure 6:
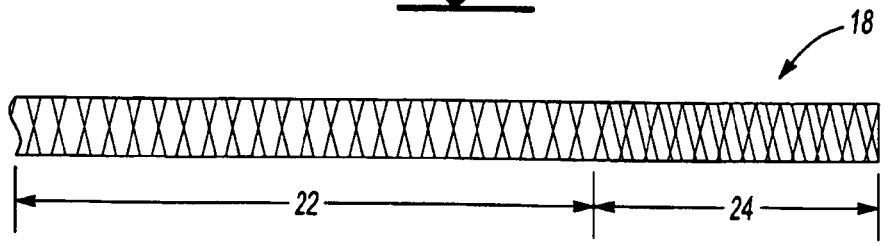
FIG. 6 is a side view of another exemplary embodiment of the feature portion of the device shown in FIG. 1.

Referring to FIG. 1, the fiber 10 includes a non-feature portion 16 and a feature portion 18. The fiber 10 is generally comprised of a core located inside of a cladding layer of a lower refractive index, so light traveling through such core is guided through total reflexion at the boundary between the cladding and the core. The feature portion 18 includes features 20 that cause interruption of the total reflexion light guiding scheme of the device 100 and force the light to couple out radially from the device 100 to provide a desired illumination pattern for photodisinfection (e.g., a generally more uniform, homogenous, and diverging radial light distribution pattern). Using art-disclosed means, the features 20 can be a variety of patterns made (e.g., cut or the like) into the fiber 10, including but not limiting, to threads or radial cuts, axial cuts, the patterns shown in FIGS. 2-6, or the like. These features 20 must break through any cladding of the fiber 10. Also, cladding of the feature portion 18 can be optionally completely removed. The depth of each of the features 20 impacts the amount of light that is coupled out at such specific feature 20. For example, the depth of each feature may range from about 0.1% to about 25% of the diameter of the fiber 10. Generally, the deeper is the specific feature 20 is made into the fiber 10 (i.e., feature's depth), the more light is coupled out at such feature 20. The frequency of a specific feature 20 (i.e., the distance between each of the features within the feature portion 18) can be varied throughout in order to vary the radial light output gradually along the feature portion 18. For example, depending upon the length of the feature portion 18, the frequency may range from about 0.01 mm to about 10 mm, from about 0.1 mm to about 1 mm, from about 0.01 mm to about 5 mm, etc. Sections of different feature frequencies (see 22 and 24) within the feature portion 18 are also possible as shown in FIG. 6. These variances 22, 24 in the features 20 allow the radial light output pattern of the device 100 to be easily adapted to specific needs, for example a constant radial light output pattern or a varying radial light output pattern. Furthermore, the light output pattern of the device 100 can be further optionally modified by having a range of different geometries such as flat, concave or convex conic (including all variants from full to truncated), hemisphere with an apex cone, or a combination thereof for the distal end 16 of the fiber 10.

Figure 7:
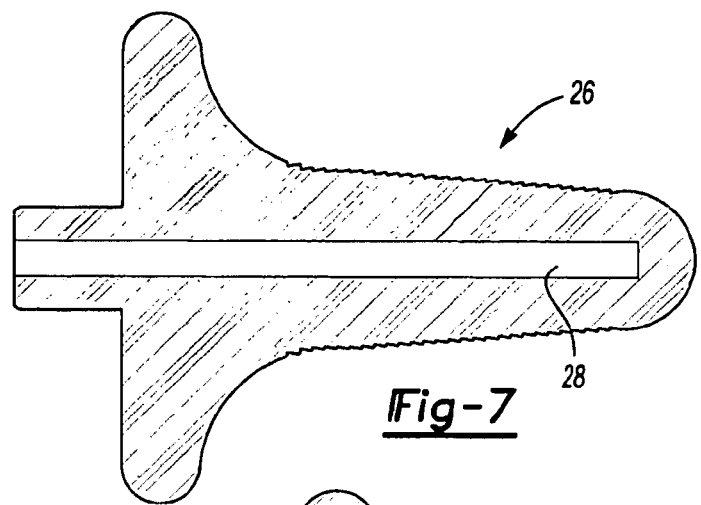
FIG. 7 is a sectional view of a light diffusing member that can optionally be included in the device shown in FIG. 1.
Figure 8:
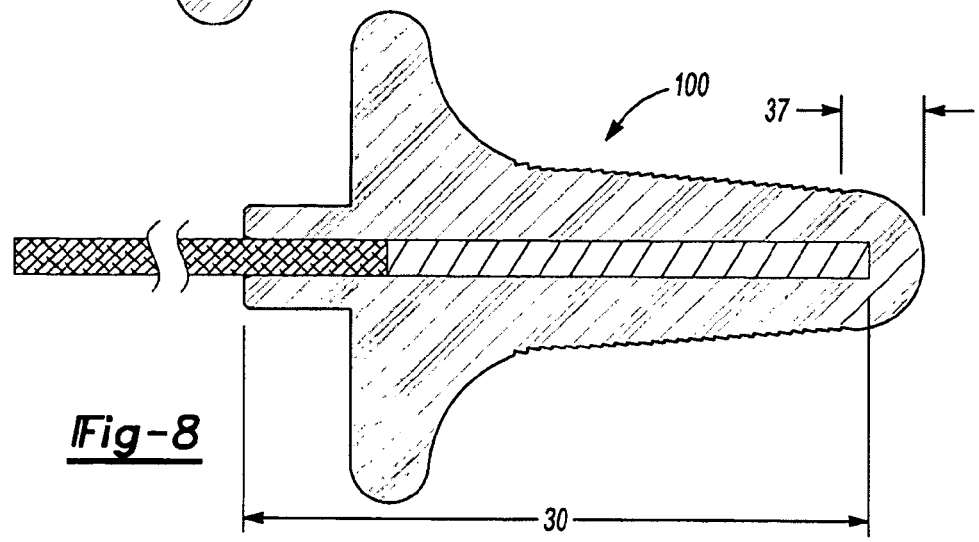
FIG. 8 is a sectional view of another exemplary embodiment of a device according to the present invention which includes the light diffusing member shown in FIG. 7.

The device 100 may optionally further includes a light diffusing member 26 shown in FIG. 7. The member 26 includes a pocket 28 adapted to accept and contain the insert portion 30 of the fiber as shown in FIGS. 7 and 8. The member 26 can be constructed out of any suitable art-disclosed material that is transparent or translucent to the illumination wavelengths. Examples of such materials are plastic, epoxy, glass, or any other suitable biocompatible material. As an example, the member 26 can be made out of polycarbonate, acrylic or Poly(methyl methacrylate).

Referring to FIG. 8, the fiber 10 may be attached to the member 26 via art-disclosed means. For example, the pocket 28 may have features (not shown) that grip the insert portion 30 (e.g., inward pointing teeth that accepts the insertion of the fiber 10 but resist its removal, threads, or the like). The insert portion 30 may also be held in by adhesive, mechanical deformation (e.g., crimping, heat staking), friction, or the like. Furthermore, the fiber 10 may be designed to be removably attached to the member 26. For example, a ferrule of some type may be attached to proximal end 32 of the insert portion 30. The ferrule can be constructed of any suitable art-disclosed material(s) such as ceramic, metal, plastic, or the like. The ferrule can be retained permanently or be removable. The ferrule may be part of the insert portion 30 or part of the member 26. Without limitation, various threaded engagements or "twist and lock" bayonets may be employed to retain the insert portion 30 within the member 26 until it is desired to remove it.

Figure 9:
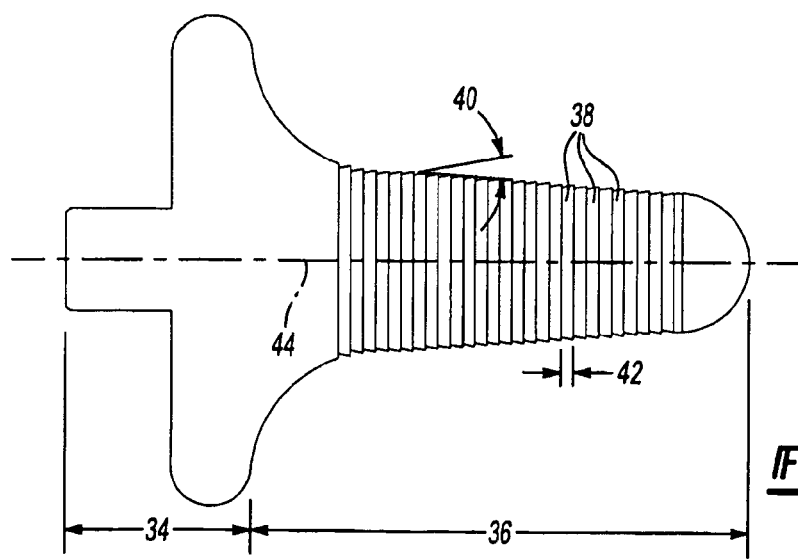
FIG. 9 is a side view of the light diffusing member of the device shown in FIG. 8.

Referring to FIG. 9, the light diffusing member 26 includes a base portion 34 and a body portion 36 adapted for insertion into a body cavity (e.g., anterior nares). To avoid potential injury to a patient, it is preferred that at least the body portion 36 does not contain any sharp corner and/or sharp edge. The front section 37 of the member 26 is part of the body portion 36 as shown in FIG. 8. The front section 37 has a flat and smooth surface. The base portion 34 is wider than the insert portion 36 and can optionally serve as a handle allowing easy handling. The base portion 34 also optionally serves as a stopper in that it stops insertion of the member 26 at a predetermined location. The base portion 34 can optionally reduce and/or prevent any photosensitizing composition from leaking out of a cavity (e.g., nasal cavity) during photodisinfection. The insert portion 36 allows for deeper insertion of the device 100 into a cavity while it eases such insertion with the smooth front section 37.

The shape of the front section 37 is designed to diverge any light coming out it. In one embodiment, this diverging light output pattern is further assisted by having the insert portion 30 and the pocket 28 extend into the front section 37 as shown in FIG. 8. As discussed in Example I below, this design not only provides a more uniform light output pattern, but it also avoids potential "hot spots".

The light output pattern of the device 100 may optionally be further impacted by geometry and/or surface finish of the member 26. For example, the member 26 may include suitable art-disclosed surface finishes such as smoothness, roughness, ribs, inclusions, pigments, microspheres, facets, embossed patterns, or a combination thereof to modify the light output pattern (e.g., light scattering or the like) of the device 100 during photodisinfection.

In one embodiment of the member 26 as shown in FIG. 9, the body portion 36 includes ribs 38 that assist in allowing illumination to be radially distributed uniformly down the length of the body portion 36. Each rib 38 is constructed out of a wedge angle 40. The wedge angle 40 shown in FIG. 9 is about 17 degree and rib width 42 ranges from about 0.48 mm to about 0.50 mm. In another embodiment, the wedge angle 40 is continuously variable and the average rays delivered from the device 100 strike at normal incidence. Other examples of the wedge angle 40 have ranges from about 13 degree to about 33 degree and from about 15 degree to about 24 degree. Other examples of rib width 42 are from about 1.5 mm to about 0.25 mm and from about 0.45 mm to about 0.55 mm. As shown in FIG. 9, the ribs 38 are rotated around the center line 44 of the member 26. The wedge angle 40 of each rib 38 is set so that the average ray that strikes the sidewall of the body portion 36 encounters a normal incidence output face and is emitted without significant refraction or redirection. The other face of each rib 38 is chosen to be parallel to the average ray angle so as to minimize the amount of internal scattering, maximizing the amount of desired radial light output for photodisinfection.

It is contemplated that a photosensitizing composition is separately delivered rather than through the device 100. For example, a syringe or a tube and pump assembly may be employed to deliver the photosensitizing composition. Applying the photosensitizing composition to treatment site may be accomplished by any art-disclosed suitable technique. To a certain extent, the application technique will depend on the viscosity of the photosensitizing composition. Liquid compositions with relatively low viscosities may be sprayed into place, while higher viscosities liquids, solids and/or pastes may be brushed, dabbed or swabbed into place. Dry films of the composition may be manually placed in the treatment site.

Depending on the material chosen to construct the device 100, the device 100 can be disposable, reusable and/or autoclavable. The device 100 can be packaged in a sterile environment. For example, the device 100 can be sealed with a hermetic cap.

The device 100 can optionally incorporate delivery of a photosensitizing composition. For example, the fiber 10 can be a hollow fiber that not only delivers light but also delivers a photosensitizing composition from a photosensitizing composition source to the treatment area.

Figure 10:
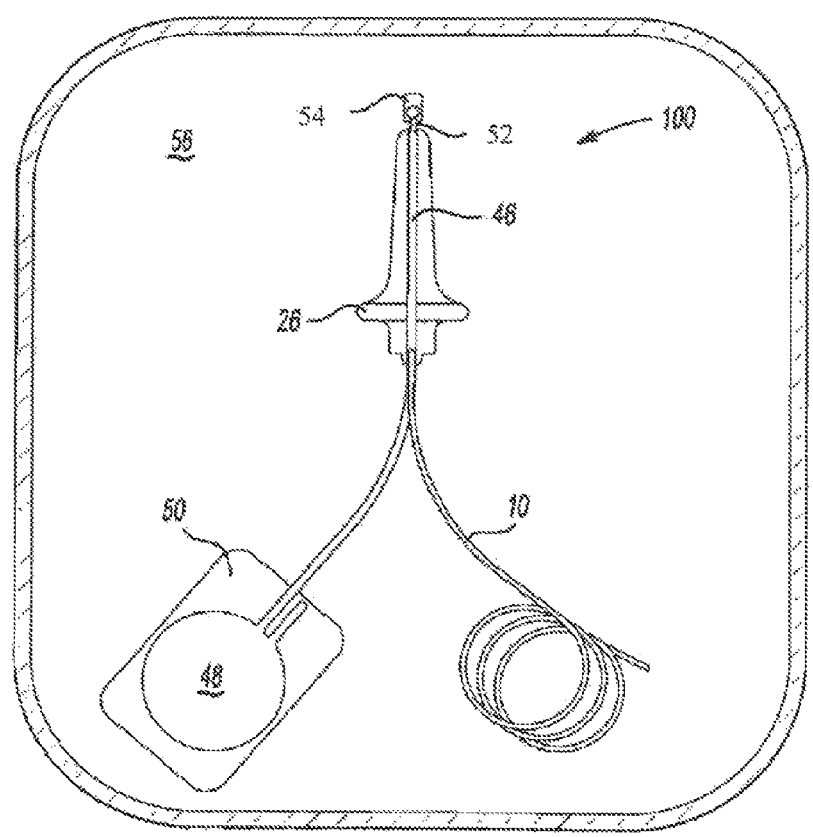
FIG. 10 is a sectional view of another exemplary embodiment of a device according to the present invention.

Another embodiment of the device 100 is shown in FIG. 10. In this embodiment, the member 26 of the device 100 can further include at least one tubular member 46 configured for fluid delivery of a photosensitizing composition 48. The tubular member 46 is in fluid communication with a photosensitizing composition source 50. The photosensitizing composition source 50 can be any art-disclosed container (e.g., a pump, a squeeze bulb, a syringe, or the like). When the photosensitizing composition source 50 is activated, the photosensitizing composition 48 will travel through the at least one tubular member 46 to opening(s) 52 and emit into the treatment area. If desired, the opening(s) 52 can optionally each include (i) an atomizing (e.g., spraying or the like) nozzle (not shown) and/or (ii) an optional removable (e.g., twist off/snap off) tip 54. Finally, the device 100 can optionally be packaged in a sterile package 56 and made available as a disposable device as illustrated in FIG. 10.

As discussed above, depending on the desired application of photodisinfection, the device 100 can be modified and/or adapted to change the ergonomics and/or the light output pattern. For example, the device 100 can be made smaller to provide an ergonomic fit within body cavities such as ear, vagina, lung, the entire digestive track (e.g., throat, esophagus, stomach, intestines, rectum, or the like) and any open wound cavity. In another example, the device 100 can be made even smaller to allow entry into body cavities that may have restricted entry or opening such as gall bladder, bladder, blood vessels, or the like. It can be appreciated that one skilled in the art can use the present invention in numerous other applications not expressly listed in this paragraph to reduce and/or eliminate microbes in a cavity.

Unless stated otherwise, dimensions and geometries of the various structures depicted herein are not intended to be restrictive of the invention, and other dimensions or geometries are possible. Plural structural components can be provided by a single integrated structure. Alternatively, a single integrated structure might be divided into separate plural components. In addition, while a feature of the present invention may have been described in the context of only one of the illustrated embodiments, such feature may be combined with one or more other features of other embodiments, for any given application. It will also be appreciated from the above that the fabrication of the unique structures herein and the operation thereof also constitute methods in accordance with the present invention. It is preferred that the components of the treatment kit are placed in sterile package(s).

B. Treatment Kit

The present invention includes a treatment kit for photodisinfection of a body cavity including the device 100, the photosensitizing composition 48 contained in the photosensitizing composition source 50. The photosensitizing composition source 50 may optionally further includes an application tip. The application tip is coupled to the syringe, a squeeze blob, or a tube and pump to deliver the photosensitizing composition 48 into the treatment area. The application tip can be any art-disclosed application tip. Examples of such application tip include self-saturating swabs (without and without custom fille—Product Numbers 4545 and 4620) manufactured by Puritan® Medical Products LLC Company located in Guilford, Maine.

It is preferred that most, if not all, of the components of the treatment kit are suitable for single use (i.e., constructed of disposable materials). The fiber 10 can be connected to the light source via an art-disclosed connection. See e.g., U.S. patent application Ser. No. 11/876,376 filed on Oct. 22, 2007 titled "Waveguide Connection Device."

Figure 11:
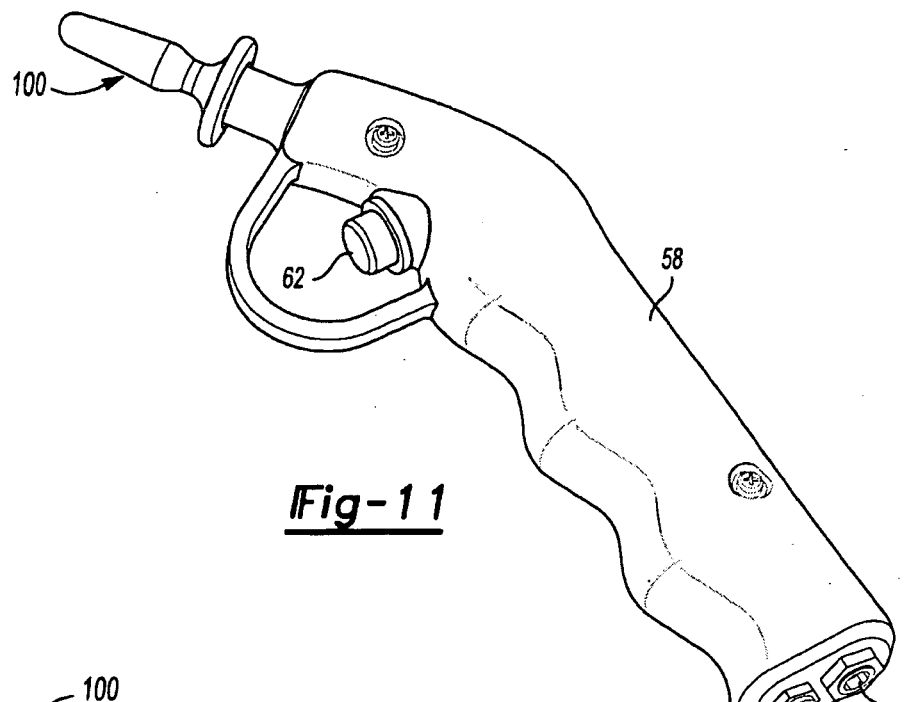
FIG. 11 is a side view of yet another exemplary embodiment of a device according to the present invention including an exemplary holder.
Figure 12:
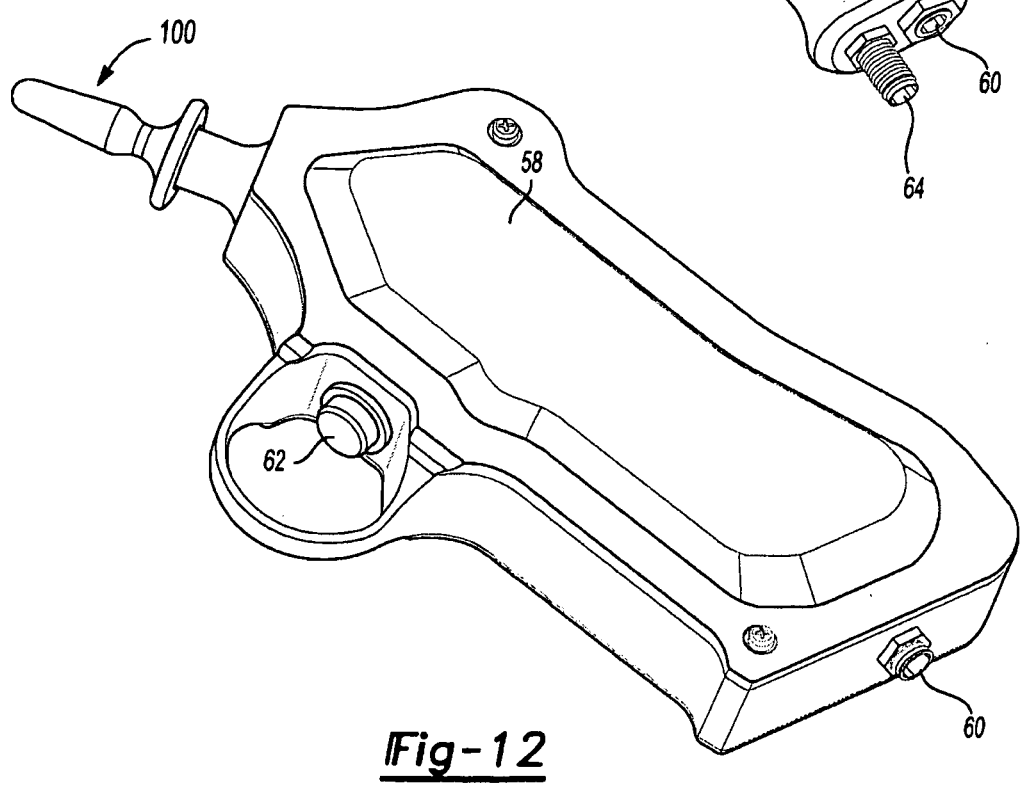
FIG. 12 is a side view of another exemplary embodiment of a device according to the present invention including another exemplary holder.
Figure 13:
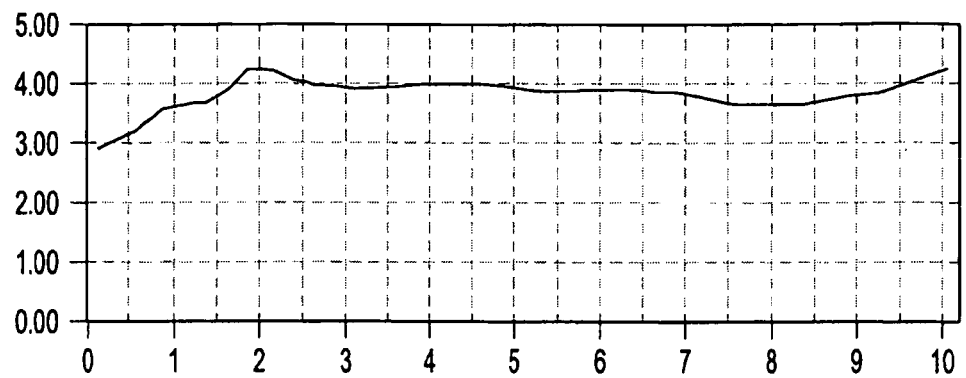
FIG. 13 is a graph showing the radial light distribution pattern for the exemplary device according to the present invention described in Example I at 0°.
Figure 14:
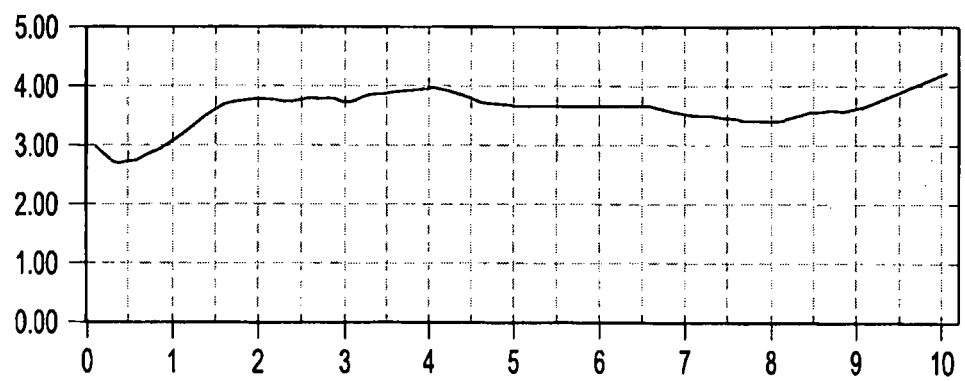
FIG. 14 is a graph showing the radial light distribution pattern for the exemplary device according to the present invention described in Example I at 90°
Figure 15:
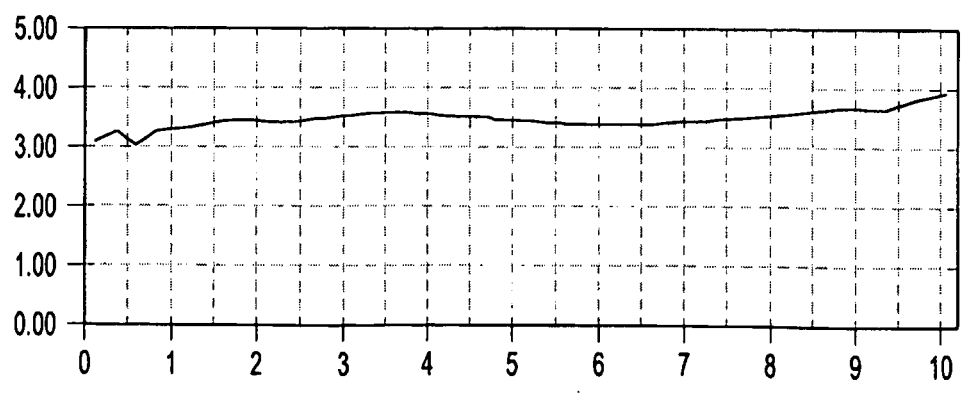
FIG. 15 is a graph showing the radial light distribution pattern for the exemplary device according to the present invention described in Example I at 180°.

In another embodiment of the present invention and referring to FIGS. 11 and 12, the device 100 further optionally includes a holder 58. The holder 58 may optionally includes: (1) a communication port 60 for light communication between the fiber 10 and the light source via a fiber optical cable (not shown); (2) a switch 62 for controlling the light input of the device 100; and/or a fluid communication means 64 (shown in FIG. 11) for fluid communication between the device 100 and the photosensitizing composition source 50.

The present invention provides an inexpensive light delivery device that can be easily mass-produced and yet still provide a more uniform radial light output pattern that is especially useful for photodisinfection of a cavity, such as a body cavity.

The present invention also provides a method to make a light delivery device comprising: providing an optical fiber having a non-feature portion and a feature portion; cutting features into the feature portion wherein the features are adapted to force light to couple out radially from the feature portion in a desired radial light output pattern.

C. Method for Photodisinfection of a Cavity

The present invention includes a method for photodisinfection of a cavity comprising applying a photosensitizing composition to treatment site within the cavity. The method further includes inserting the device 100 described above into the cavity and applying light delivered by the device 100 to the treatment site at a wavelength absorbed by the photosensitizing composition so as to inhibit or eliminate microbes located in the treatment site.

The present invention further includes a method for photodisinfection of a cavity comprising inserting the device 100 described above into the cavity and applying a photosensitizing composition and light to a treatment site wherein both the photosensitizing composition and light are both delivered by the device 100 to the treatment site and the light is at a wavelength absorbed by the photosensitizing composition so as to inhibit or eliminate microbes located in the treatment site. When the present invention is in use, the photosensitizing composition source delivers the photosensitizing composition to the device 100, which is configured for dispensing light in a desired light output pattern to the treatment area. The method can be performed by (1) applying the photosensitizing composition first and then the light; or (2) applying the photosensitizing composition and the light simultaneously. Depending on the nature and extent of the microbes located at the treatment site, the practitioner may apply multiple cycles of light applications (e.g., about 2 to about 10, about 3 to about 5, etc.) to the treatment site or the entire method can be repeated multiple times (e.g., about 2 to about 10, about 3 to about 5, etc.) until the desired effects have been reached.

As discussed above, the light required for these methods are delivered to the device 100 by the light source via the fiber 10 described above. When used for photodisinfection of a body cavity, it is preferred that the application of light does not cause physiological damage to host tissue at and surrounding the treatment site.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes.

The following example provided in accordance to the present invention is for illustrative purpose only and is not intended as being exhaustive or limiting of the invention.

EXAMPLE I

Another exemplary embodiment of the device 100 of the present invention is provided with the following size and dimensions. The member 26 of this embodiment is constructed out of plastic such as a clear acrylic, PMMA, or the like. The member 26 is formed by art-disclosed injection molding process. The member 26 has a total length of about 28 mm and a width (measured at its widest part) of about 19 mm. The body portion 36 includes ribs 38. The wedge angle 40 is about 17 degree and the rib width 42 ranges from about 0.48 mm to about 0.50 mm. The pocket 28 of the member 26 is sized to contain the insert portion 30 in its entirety.

The fiber 10 is a low cost plastic fiber with a diameter of about 1.1 mm (e.g., a 1 mm plastic fiber). The insert portion 30 has a total length of about 26 mm. The cladding of about 17 mm of the insert portion 30 measuring from the distal end 12 of the fiber 10 has been removed and the feature portion 18 is located within this non-clad portion of the insert portion 30. The feature portion 18 measuring from the distal end 12 of the fiber has a total length of about 10 mm and has the same features 20 as shown in FIG. 1. The features 20 are threads or radial cut into the feature portion 18 at a frequency of about 0.5 mm and about 0.05 mm in depth.

Both the pocket 28 and the insert portion 30 are extended into the front section 37 of the member 30. The front section 37 has an outside radius of about 2.8 mm. The proximal end 12 of the fiber 10 is placed in the front section 37 at a location that is less than the focal length of its outside radius (e.g., about 2.8 mm in this example) which acts as a positive lens, thereby allowing a diverging light output pattern. This diverging light output pattern avoids "hot spots" in the treatment area and reduces the power density of the device's 100 light output. If the light source for the device 100 is a laser, then this reduction in power density will lower the safety classification for this laser-powered device 100. A lower laser safety classification will reduce and/or eliminate the need for expensive safety features, which are often required for a higher power density laser device.

Figure 16:
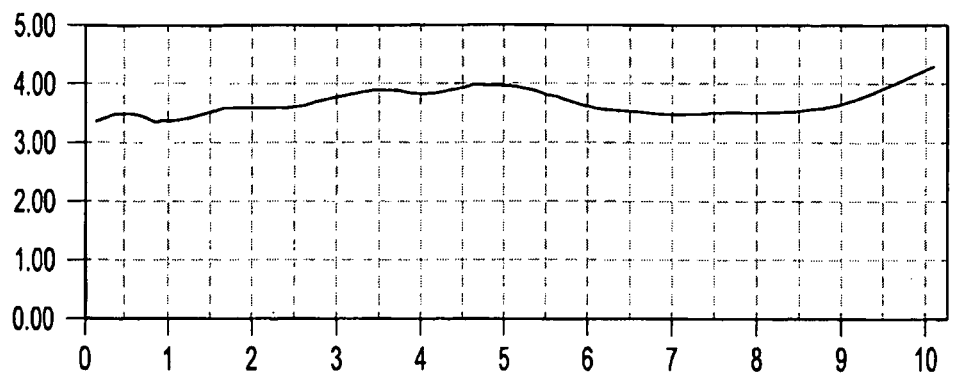
FIG. 16 is a graph showing the radial light distribution pattern for the exemplary device according to the present invention described in Example I at 270°.
Figure 17:
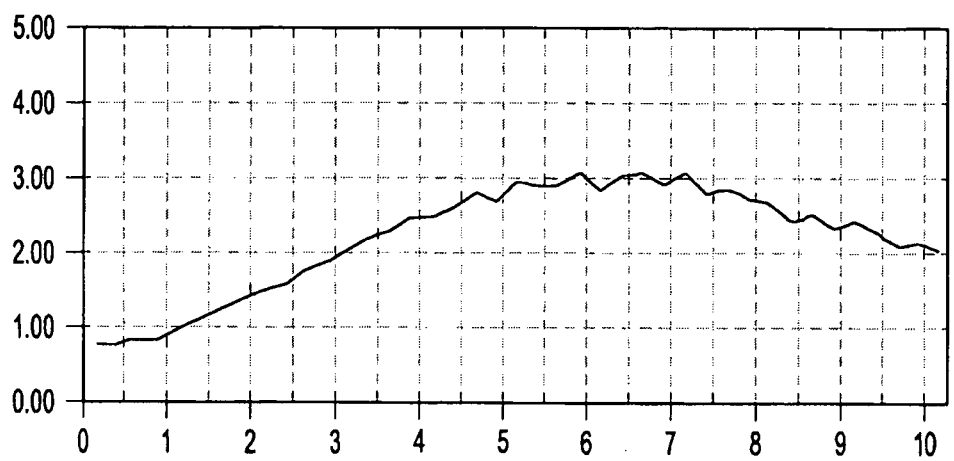
FIG. 17 is a graph showing the radial light distribution pattern of the PAD at 0°.
Figure 18:
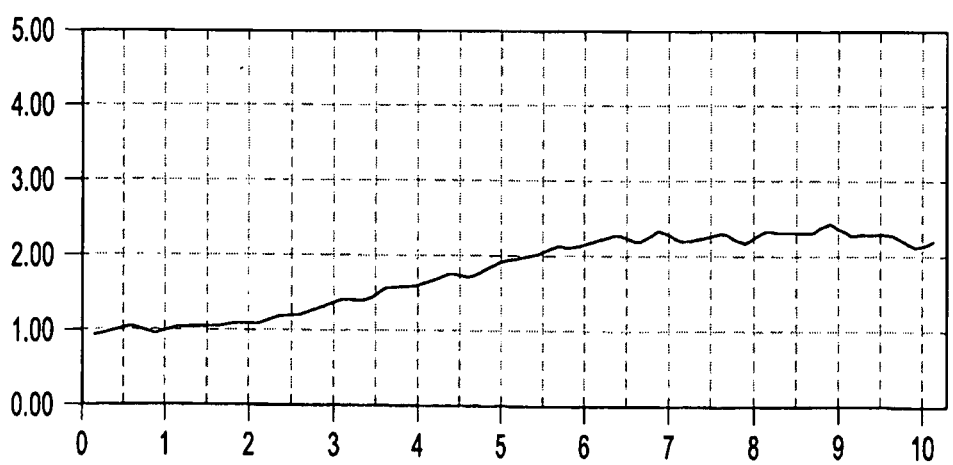
FIG. 18 is a graph showing the radial light distribution pattern of the PAD at 90°.
Figure 19:
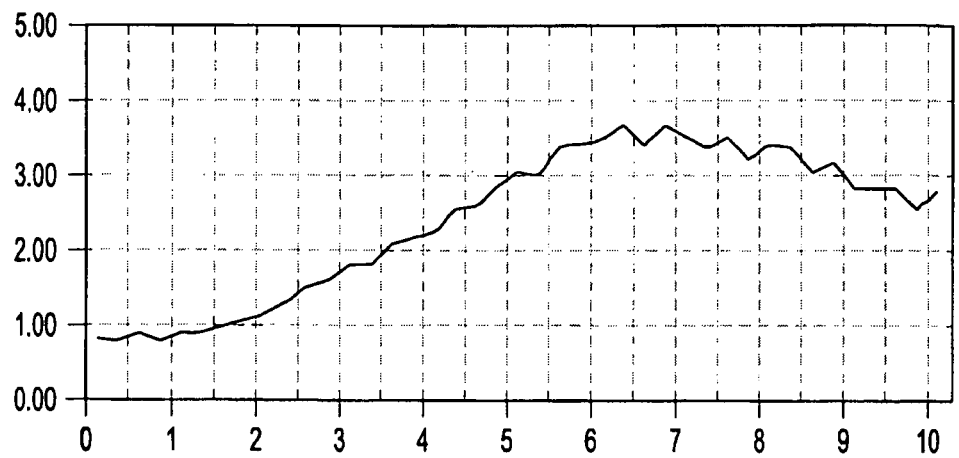
FIG. 19 is a graph showing the radial light distribution pattern of the PAD at 180°.
Figure 20:
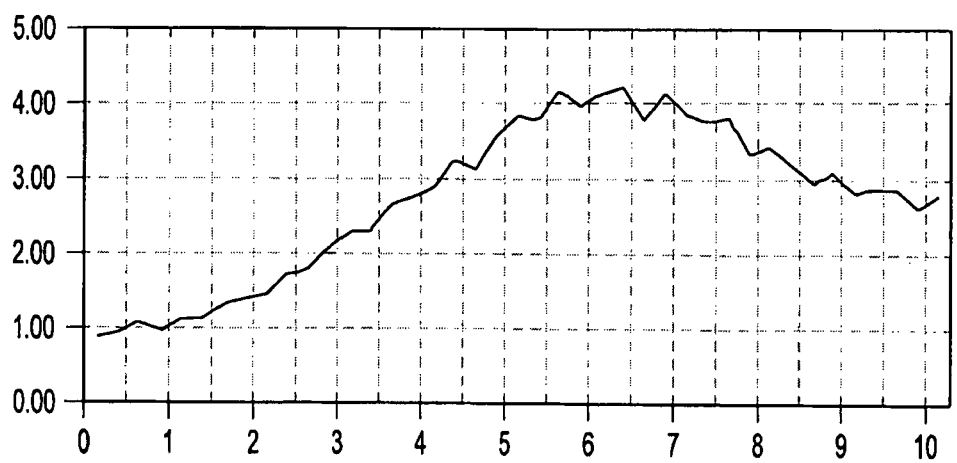
FIG. 20 is a graph showing the radial light distribution pattern of the PAD at 270°.

To demonstrate that the device 100 as described in Example I provides a more optimal light output pattern for photodisinfection (e.g., a more uniform radial light output pattern), it was tested against a prior art light delivery device described in U.S. Patent Application Publication No. US2007/0255356 at paragraph nos. 73-75 and FIGS. 16-18 ("PAD"). The PAD had a light diffusing member that was the same in exterior size and shape as the member 26 described in Example I. The PAD did not have the feature portion 18. Instead, the PAD has a light dispersing section within its pocket of its member that impacts its light output pattern. The PAD's light dispersing section was shaped like a hemisphere with an apex cone. See paragraph no. 73 of U.S. Patent Application Publication No. 2007/0255356.

The device 100 as described in Example I was connected to a diode laser Alplight AG Model HPL-1 with an optical power of 1.2 W at a wavelength of 670 nm and tested by turning it by 0°, 90°, 180°, and 270° about its respective optical axis in order to determine rotation symmetry of its respective radial light output patterns for the feature portion 18. The radial light output pattern of the feature portion 18 of the device 100 at 0°, 90°, 180°, and 270° are respectively provided in FIGS. 13-16. FIGS. 13-16 show the light power intensity (vertical scale of arbitrary units) throughout the length of the feature section (horizontal scale of mm).

The PAD was also connected to the same laser and tested by turning it by 0°, 90°, 180°, and 270° about its respective optical axis in order to determine rotation symmetry of its respective radial light output patterns for the about 10 mm region of its light diffusing member that corresponds to the feature portion 18 of the device 100. The radial light output pattern of this about 10 mm corresponding region of the PAD at 0°, 90°, 180°, and 270° are respectively provided in FIGS. 17-20. FIGS. 17-20 show the light power intensity (vertical scale of the same arbitrary units as used in FIGS. 13-16) throughout the length of the region that corresponds to the feature section 18 of the device 100 (horizontal scale of mm).

FIGS. 13-20 show that the device 100 provided a more uniform radial light output pattern because it distributed more light out of its sides radially down the full length of the feature portion 18 of the member 26 with less light coming out of the front section 37 when compared to the PAD. This is further supported by the following measurements made of the device 100 and the PAD. The total light output ("$P_{total}$") and the light output of the front sections (e.g., 37) ($P_{front}$) of both the device 100 and the PAD were measured and calculated to determine their respective ratios ("$R_p$") wherein $R_p$ 32 $P_{front}/P_{total}$. The Rp for the PAD was 29%. The Rp for the device 100 was 18%, which shows that less light is exiting the front section and more light is exiting radially, which is beneficial to the treatment efficacy.

To demonstrate that the device 100, as described in Example I, provides a lower laser safety classification, measurements based upon the Laser Safety Standard IEC 60874-1 (second edition 2007-03), page 103, Table 11, Output of Measuring Condition 3 (i.e., light power intensity through a 7 mm aperture in a distance of 100 mm) were made for both the device 100 and the PAD. Both the PAD and the device 100 were each connected to a diode laser Alplight AG Model HPL-1 with an optical power of 1.2 W at a wavelength of 670 nm. The light power intensity through a 7 mm aperture in a distance of 100 mm was measured for each of them. The light power intensity was 2.7 mW for the PAD and only 432 pW for the device 100. This low power intensity allows that device 100 to have a laser safety classification of Class 2 or lower.

What is claimed is:

1. A light delivery device comprising an optical fiber having;
    (i) a core and a cladding layer that covers at least a portion of the core, wherein the cladding layer has a lower refractive index than that of the core; and
    (ii) a non-feature portion of the optical fiber; and (iii) a feature portion of the optical fiber having features that force light to couple out radially from the feature portion and provide a desired diffused radial light output pattern wherein:
  (a) the core of the feature portion is circumferentially covered by the cladding layer;
  (b) the features are selected from the group consisting of threads, radial cuts, axial cuts, and a combination thereof; and
  (c) at least a portion of the core of the feature portion and at least a portion of the cladding layer of the feature portion contain the features wherein each of the features is made into both the cladding layer and the core located directly beneath the cladding layer.

2. The light delivery device of claim 1 wherein the features are radial cuts.

3. The light delivery device of claim 1 wherein amount of light radially from each of the features is impacted by depth of each of the features that has been made into the optical fiber.

4. The light delivery device of claim 3 wherein the depth of each of the features ranges from 0.1% to 0.25% of diameter of the optical fiber.

5. The light delivery device of claim 1 wherein distance between each of the features is varied within the feature portion.

6. The light delivery device of claim 1 wherein distance between each of the features within the feature portion ranges from 0.01 mm to 10 mm.

7. The light delivery device of claim 1 wherein distal end of the optical fiber has a geometry selected from a group consisting of flat, concave conic, convex conic, hemisphere with an apex cone, and a combination thereof.

8. The light delivery device of claim 1 wherein the optical fiber is a polymer optical fiber.

9. The light delivery device of claim 1 wherein the optical fiber has a diameter ranges from 50 µm to 3 mm.

10. The light delivery device of claim 1 further comprising a light diffusing member having a pocket adapted to accept an insert portion of the optical fiber.

11. The light delivery device of claim 10 wherein the light diffusing member (i) is plastic, (ii) is formed by injection molding process, (iii) has a body portion containing ribs; and is removably attached to the optical fiber.

12. The light delivery device of claim 1 wherein (i) the cladding layer does not cover distal end of the optical fiber including a length of 17 mm of the optical fiber measuring from the distal end; (ii) the features are threads cut into the optical fiber at a period of 0.5 mm and at a depth of 0.05 mm.

13. The light delivery device of claim 1 further comprising a light source in light communication with the optical fiber wherein the desired radial light output pattern is in the visible range.

14. The light delivery device of claim 13 wherein the light source is a laser.

15. The light delivery device of claim 1 wherein the features are threads cut into the optical fiber at a period of 0.5 mm and at a depth of 0.05 mm.

16. The light delivery device of claim 1 wherein the features are axial cuts.

17. The light delivery device of claim 1 wherein the features are threads.

18. A method of photodisinfection of a cavity comprising:
(a) providing a light delivery device comprising an optical fiber having: (i) a core and a cladding layer that covers at least a portion of the core, wherein the cladding layer has a lower refractive index than that of the core; and (ii) a non-feature portion of the optical fiber and a feature portion of the optical fiber having features that force light to couple out radially from the feature portion and provide a desired diffused radial light output pattern wherein:
  (1) the core of the feature portion is circumferentially covered by the cladding layer;
  (2) the features are selected from the group consisting of threads, radial cuts, axial cuts, and a combination thereof; and
  (3) at least a portion of the core of the feature portion and at least a portion of the cladding layer of the feature portion contain the features wherein each of the features is made into both the cladding layer and the core located directly beneath the cladding layer;
(b) applying a photosensitizing composition to treatment site within the cavity;
(c) inserting at least a portion of the device into the cavity; and
(d) applying light delivered by the device from a light source to the treatment site within the cavity at a wavelength absorbed by the photosensitizing composition so as to inhibit or eliminate microbes located at the treatment site.

19. The method of claim 18 wherein the light delivery device further comprising a light diffusing member having a pocket adapted to accept an insert portion of the optical fiber.

20. A light delivery device comprising a polymer optical fiber having;
(i) a core and a cladding layer that covers at least a portion of the core, wherein the cladding layer has a lower refractive index than that of the core; and
(ii) a non-feature portion of the polymer optical fiber; and
(iii) a feature portion of the polymer optical fiber having features that force light to couple out radially from the feature portion and provide a desired diffused radial light output pattern wherein:
  (a) the core of the feature portion is circumferentially covered by the cladding layer;
  (b) the features are selected from the group consisting of threads, radial cuts, axial cuts, and a combination thereof; and
  (c) at least a portion of the core of the feature portion and at least a portion of the cladding layer of the feature portion contain the features wherein each of the features is made into both the cladding layer and the core located directly beneath the cladding layer.

21. The light delivery device of claim 20 wherein the features are threads.

22. The light delivery device of claim 20 wherein the features are radial cuts.

23. The light delivery device of claim 20 wherein the features are axial cuts.

24. The light delivery device of claim 20 wherein distance between each of the features is varied within the feature portion.

25. The light delivery device of claim 20 further comprising a light diffusing member having a pocket adapted to accept an insert portion of the optical fiber.

* * * * *